US00PP23623P3

(12) United States Plant Patent
Egger

(10) Patent No.: US PP23,623 P3
(45) Date of Patent: May 21, 2013

(54) *AGASTACHE* PLANT NAMED 'SUMMER SUNSET'

(50) Latin Name: ***Agastache* spp.**
Varietal Denomination: Summer Sunset

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 96 days.

(21) Appl. No.: 13/200,486

(22) Filed: Sep. 22, 2011

(65) Prior Publication Data

US 2013/0081177 P1 Mar. 28, 2013

(51) Int. Cl.
*A01H 5/00* (2006.01)

(52) U.S. Cl.
USPC ..... Plt./399

(58) Field of Classification Search ..... Plt./399
See application file for complete search history.

*Primary Examiner* — Howard Locker
(74) *Attorney, Agent, or Firm* — Klarquist Sparkman, LLP

(57) ABSTRACT

A new and distinct form of *Agastache* plant characterized by orange flowers, a bushy, upright, well-branching habit, a long bloom time, and excellent vigor.

1 Drawing Sheet

Botanical denomination: *Agastache* spp.
Variety designation: 'Summer Sunset'.

BACKGROUND OF THE INVENTION

The present invention relates to a new and distinct cultivar of *Agastache*, given the name, 'Summer Sunset'. *Agastache* is in the family Lamiaceae. This new variety is an open pollinated seedling selection out of *Agastache* 'Summer Glow' as such the pollen parent is unknown.

Compared to the seed parent, *Agastache* 'Summer Glow' (U.S. Plant Pat. No. 20,980), the new cultivar has orange rather than soft yellow colored flowers and a shorter habit.

Compared to *Agastache* 'Summer Fiesta' (U.S. Plant Pat. No. 22,086), the new cultivar has flowers that are more orange than red and a shorter habit.

Compared to *Agastache* 'Apricot Sprite', an unpatented plant, the new cultivar blooms longer, has a larger habit, a darker orange flower color, and is hardier.

This plant exhibits the following characteristics that make it unique:

1. orange flowers,
2. a bushy, upright, well-branching habit,
3. a long bloom time, and
4. excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a 1 year-old *Agastache* 'Summer Sunset' growing in the trial bed in mid July in Canby, Oreg.

DETAILED PLANT DESCRIPTION

The following is a detailed description of the new *Agastache* cultivar based on observations of 6-month-old specimens in August grown outside in full sun in one gallon container in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Upright.
*Type*.—Herbaceous perennial.
*Cold hardiness*.—USDA Zone 7-10.
*Size*.—Grows to 34 cm wide and 30 cm tall to the top of the flowers.
*Vigor*.—Excellent.
*Branching*.—About 18 branches from the base.
*Stem*.—Square in cross section, grows to 4 mm wide and 12 cm tall to the first main flower, pubescent, internodes range from 2 to 4 cm long, Yellow Green 147A.
*Roots*.—White 155B, fibrous, plants root easily from stem tip cuttings.

Leaf:

*Type*.—Simple.
*Arrangement*.—Opposite.
*Shape*.—Ovate.
*Venation*.—Pinnate.
*Margins*.—Crenate.
*Apex*.—Acute.
*Base*.—Truncate.
*Blade size*.—Grows to 50 mm long and 40 mm wide.
*Surface texture*.—Pubescent on both sides.

*Petiole description*.—Grows to 34 mm long and 1 mm wide, pubescent, Yellow Green 147B.

*Leaf color*.—Top side closest to Green 137A, bottom side \Yellow Green 147B.

Inflorescence:

*Type*.—Terminal spike with about 6 whorls.

*Number of flowers*.—About 80 per spike.

*Size of inflorescence*.—Grows to 17 cm tall and 7 cm wide.

*Peduncle*.—Grows to 6 cm tall and 1 mm wide, pubescent, Yellow Green 147B.

*Pedicel*.—2 mm long, pubescent, Yellow Green 147C.

*Bloom period*.—July through frost in Canby, Oreg.

Flower bud:

*Size*.—16 mm long and 4 mm wide at the widest point prior to opening.

*Description*.—Tubular.

*Surface texture*.—Pubescent.

*Color*.—Greyed Orange N170B.

Flower:

*Type*.—Zygomorphic.

*Shape*.—Bilabiate, tubular.

*Size*.—37 mm long and 9 mm wide.

*Corolla description*.—Grows to 35 mm long and spreads to 9 mm wide; color outside Greyed Orange 168A and inside Red 39B on lobe tips to Orange 29A on lobe bases to Orange 26C in tube; glabrous inside and pubescent outside, tube 28 mm long and 1 mm to 5 mm wide; 2 upper lobes joined 4 mm long and 5 mm wide, oblong, tip acute, margin entire; three lower lobes, two spreading sideways, each 4 mm long and 3.5 mm wide, tip acute, margin entire; the bottom lobe broad, cupped, obovate, edges irregularly serrate, 7 mm wide and 4 mm deep.

*Calyx description*.—7 mm long and 3 mm wide, pubescent outside and glabrous inside, 5 lobed, lobes triangular, 2 mm long, margin entire, tip acuminate, color Greyed Green 147B.

*Pistil description*.—40 mm long, ovary 1.5 mm long, Orange White 159A, style 38.5 mm long, White NN155D; stigma Purple Violet N81A.

*Stamen description*.—4 in number, paired and exerted, top two 35 mm long and bottom two 32 mm long, filaments Purple 75A, anthers 0.5 mm long, Purple Violet N81D, pollen White 155A.

*Fragrance*.—Light herbal.

*Lastingness*.—A spike blooms for about 3 weeks on the plant.

Fruit/seed: 4 nutlets, 1 mm long, ovoid, Black 202A.

Pests and diseases: *Agastache* are known to be susceptible to downy mildew (*Peronospora*) and rust (*Puccinia*) in dry summer months. The new cultivar has no known resistances but has shown no problems in Canby, Oreg.

I claim:

1. A new and distinct form of *Agastache* plant substantially as shown and described.

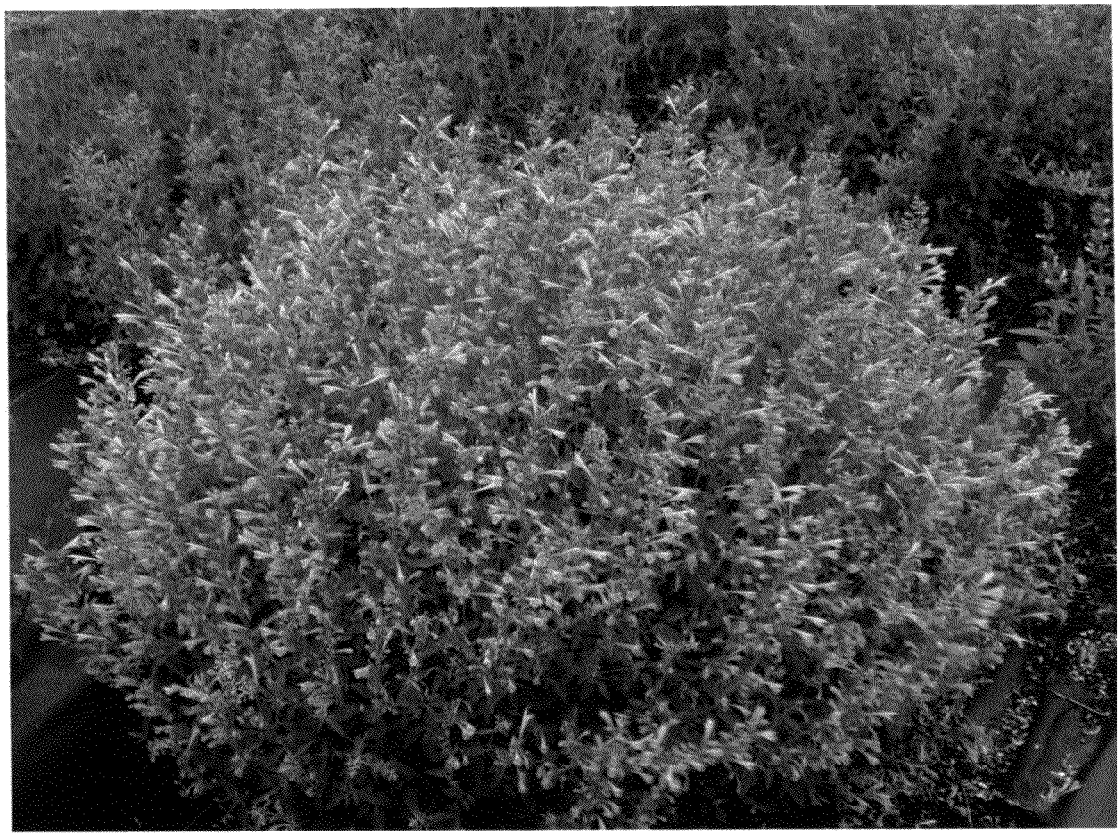

* * * * *